Figure 1:
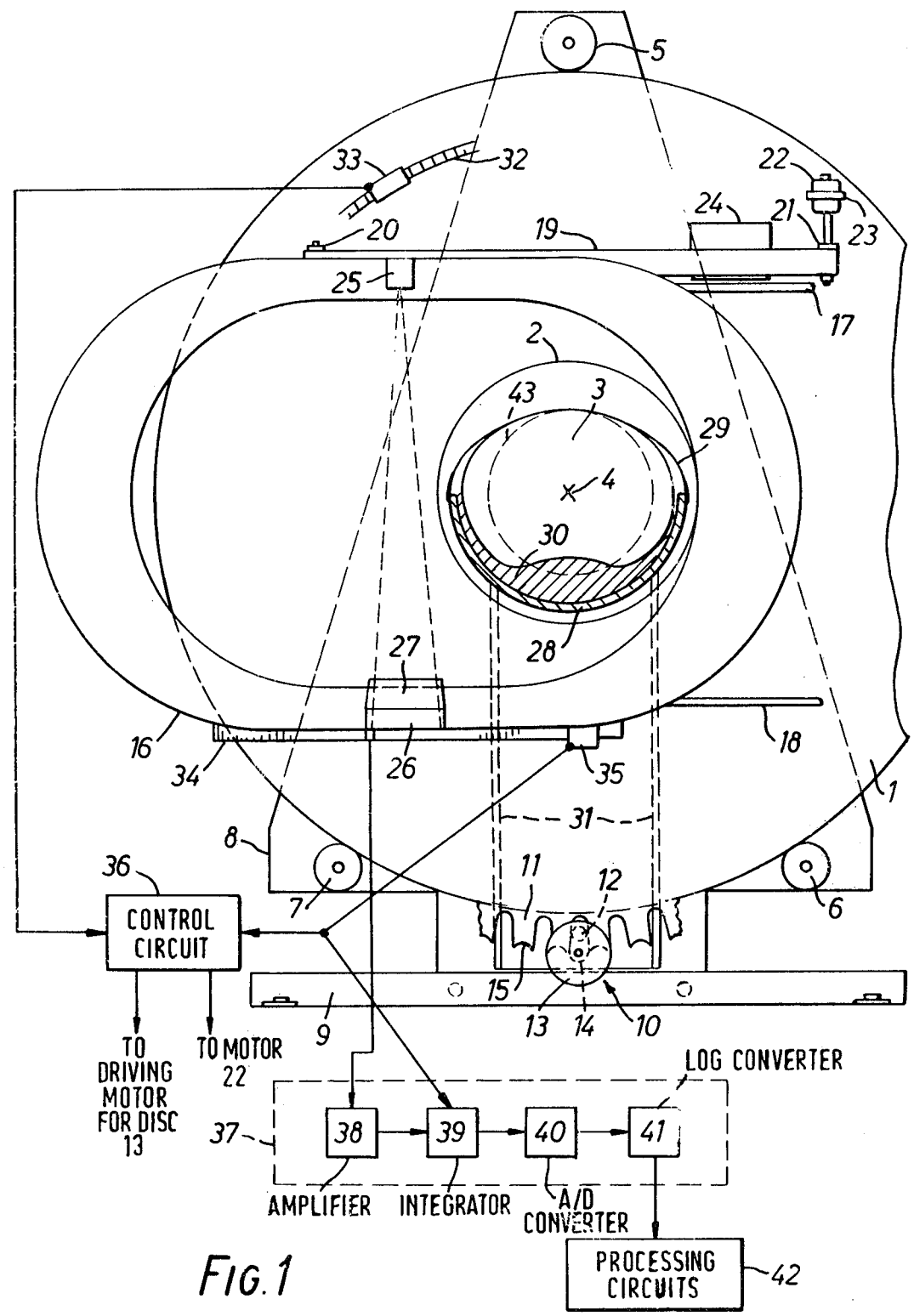

United States Patent [19]
Hounsfield

[11] 4,150,294
[45] Apr. 17, 1979

[54] RADIOGRAPHY

[75] Inventor: Godfrey N. Hounsfield, Newark, England

[73] Assignee: EMI Limited, Hayes, England

[21] Appl. No.: 735,144

[22] Filed: Oct. 26, 1976

[30] Foreign Application Priority Data

Nov. 5, 1975 [GB] United Kingdom ............ 45869/75

[51] Int. Cl.$^2$ ............................................. G03B 41/16
[52] U.S. Cl. .................................. 250/445 T; 250/360
[58] Field of Search ........... 250/445 T, 445 R, 439 R, 250/360, 363, 366

[56] References Cited

U.S. PATENT DOCUMENTS

| | | | |
|---|---|---|---|
| 3,946,234 | 3/1976 | Hounsfield | 250/445 T |
| 3,986,031 | 10/1976 | Chekrown | 250/445 T |

*Primary Examiner*—Craig E. Church
*Attorney, Agent, or Firm*—Cooper, Dunham, Clarke, Griffin & Moran

[57] ABSTRACT

In a computerized tomographic apparatus, a scanning device is used to project radiation through a slice disposed cross-sectionally of a body along many sets of pencil-like beam paths. Each set of paths is characterized by being oriented at a respective angle, or in some circumstances a respective mean angle, in the slice. The absorption suffered by the radiation on traversing each beam path is measured and, from all the values of absorption, the coefficient of absorption of the radiation at each of many locations distributed over the slice is calculated. The invention extends the number of paths in some only of the aforementioned sets to include further paths traversing a zone outside the slice and the absorption values relating to these further paths are used to improve the accuracy of the calculation of the coefficients of absorption.

7 Claims, 2 Drawing Figures

RADIOGRAPHY

The present invention relates to radiography, and it relates especially, though not exclusively, to radiographic apparatus by means of which it is possible to determine the absorption or transmission coefficients at a plurality of locations distributed over a slice cross-sectionally disposed in a body under examination. An apparatus for, and method of, effecting the evaluation referred to above is described and claimed in U.S. Pat. No. 3,778,614.

The technique for such evaluation involves determining the amount of radiation absorbed on traversing each of a large number of linear paths through the slice and processing the absorption values so determined in accordance with a compensated layergram operation. In order to project the radiation through the body along all of the aforementioned paths, the source of the radiation and an associated detector means are scanned relative to the body.

The aforementioned Patent discloses techniques for effecting the scanning and the processing; a faster scanning technique being described and claimed in U.S. Pat. No. 3,946,234, whereas a faster processing technique is described and claimed in U.S. Pat. No. 3,924,129.

The processing technique disclosed in the aforementioned U.S. Pat. No. 3,924,129 involves a form of convolution of the determined absorption data in which the data are assembled in sets corresponding to paths through the body and distributed across the slice; each determined absorption value is modified by being combined with the values relating to other paths of the same set, each weighted in accordance with a weighting function which decreases in amplitude with increasing distance of the path corresponding to the value being weighted from the path corresponding to the value being modified. The modified values are then superimposed in layergram format. This technique is a compensated layergram operation as mentioned previously.

The procedure described above is usually carried out in relation to a circular region of the slice which contains the parts of the body which are of interest; it being assumed that features disposed in the plane of the slice but outside the region of interest can be ignored. It has now been discovered that the assumption referred to above is not completely justified in all circumstances and that it is possible for said features to introduce errors into the evaluation of the aforementioned coefficients.

It is an object of this invention to provide radiographic apparatus including means for reducing errors of the kind referred to in the immediately preceeding paragraph.

According to the invention there is provided radiographic apparatus including means for projecting radiation through a slice of a body along a plurality of sets of beam paths, each set of paths being orientated at a respective angle or mean angle in the slice, detector means for dectecting the radiation emergent from the body along each path and processing means for processing output signals derived from said detector means and indicative of the absorption suffered by the radiation on traversing each of said paths to evaluate the absorption coefficient, with respect to said radiation, at each of a plurality of locations distributed over a predetermined region in the plane traversed by all of said paths, means being provided for obtaining further output signals, indicative of the absorption suffered by said radiation on traversing further paths, constituting an extension of the number of paths of some only of said sets, through a zone of said slice surrounding said region, and means for utilising said further output signals to compensate said evaluation for errors introduced by the passage of said radiation through said zone along paths which also traverse said region.

Figure 2:
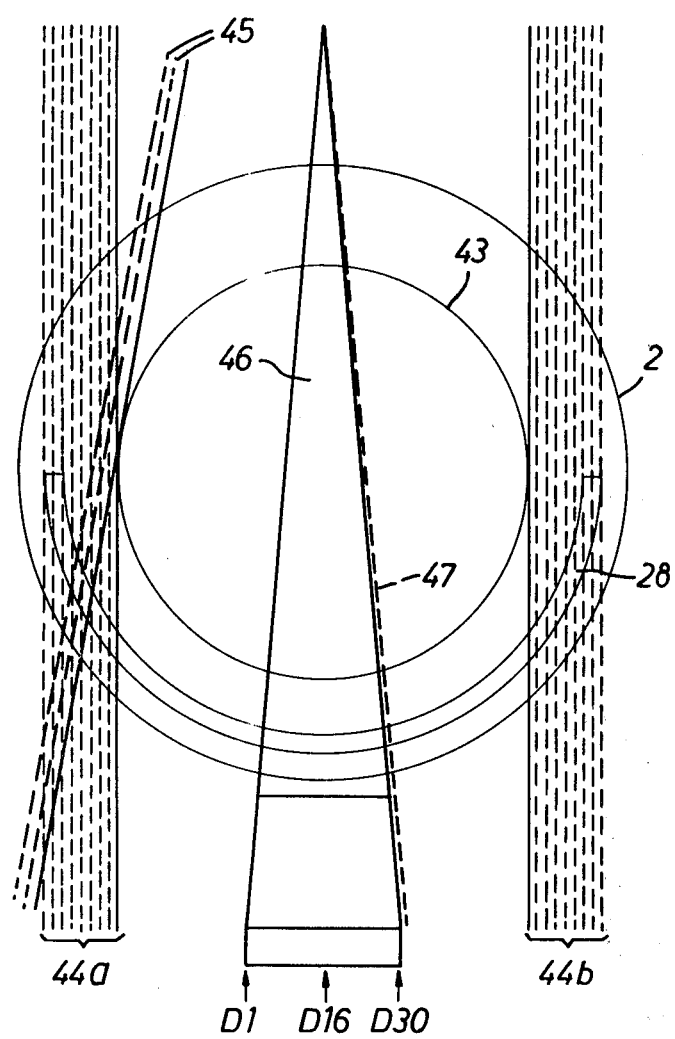

In order that the invention may be clearly understood and readily carried into effect, one embodiment thereof will now be described, by way of example only with reference to the accompanying drawings of which:

FIG. 1 shows, in front elevational view, radiographic apparatus in conjunction with which the invention may be used with advantage, and FIG. 2 shows, on enlarged scale, part of the FIG. 1 arrangement and indicates certain beam paths.

Referring now to FIG. 1, the apparatus shown therein is similar in principle to the apparatus described in the aforementioned U.S. Pat. No. 3,946,234. A turntable member 1 having a central aperture 2, to accommodate a body 3 to be examined, is mounted vertically for rotation about an axis 4 which is disposed centrally in the aperture 2. The member 1 is supported on three rotatable bearings 5, 6 and 7 which are journalled in a main frame 8 for the apparatus. The frame 8 remains stationary, being rigidly secured to a pedestal 9, and can take any suitable form, although it must of course be formed with an aperture coincident with the aperture 2.

The member 1 can be rotated in angular steps of (in this example) ten degrees by means of a Geneva mechanism generally shown at 10. The periphery of member 1 is formed with suitable prongs such as 11 which co-operate with a peg 12 on a continuously rotated disc 13 to effect the required step-wise rotary movement. The disc 13 also carries a locking cam 14 which co-operates with suitably shaped recesses such as 15 on the prongs such as 11 to effectively lock the member 1 in its angular position so long as the peg 12 is not in one of the slots formed between adjacent prongs 11. Disc 13 is journalled in the main frame 8 and is driven by an electric motor which is not shown.

Mounted upon the turntable 1, and capable of performing a reciprocating lateral scanning motion relative thereto, is a lightweight but rigid scanning yoke 16. Yoke 16 can move on linear runners 17 and 18 which are fixedly mounted on the rotatable member 1 and are disposed chordally thereof. The lateral scanning motion is imparted to the yoke 16 by virtue of a toothed belt 19, which is stretched between a pair of toothed rollers 20 and 21 journalled in respective brackets (not shown) secured to the member 1, and to which the belt the yoke 16 is attached by means of a bracket (not shown). The roller 20 is merely an idler roller, but roller 21 is driven by a reciprocating motor 22 which is attached by a strap-like bracket 23 to the member 1.

It will be appreciated that the pedestal 9 will be supported on a suitable girder or the like which ensures ground clearance of the yoke 6 in all angular positions of the turntable 1 and all lateral position of the yoke 16 thereon.

A counter-balance weight 24 is secured to the opposite run of belt 19 to the yoke 16 and thus moves in opposition thereto to compensate for out-of-balance forces which would otherwise be set up by the lateral scanning motion of the yoke 16 and its attachments, which will now be described.

Attached to the yoke 16 is a source 25 of penetrating radiation, in this example X-radiation. The radiation is collimated to form a planar, fan-shaped beam, emanating from an effective point source. On the opposite side of yoke 16, with respect to the aperture 2, to the source 25 is an array 26 of thirty detectors sensitive to the radiation generated by the source 25, each viewing the source through a respective collimator; the collimators being disposed in a bank 27. In this example, neighbouring collimators are inclined to each other at an angle of $\frac{1}{3}°$ and since there are thirty detectors, this means that the angular spread of the beam of X-rays generated by the source 25 is 10°. As will be made clear later, the beam is not symmetrical about the perpendicular line drawn from the effective point source of the beam of X-radiation to the array 26. This line is arranged to intersect the sixteenth detector in the array 26 (counting from the left).

The body 3 is supported on a bed 28 and is secured thereon by means of straps such as 29. Gaps between the body and the bed are filled with a suitable packing material 30 which is preferably of doughlike consistency and absorbs the X-radiation to substantially the same extent as does human tissue. The material 30 is preferably contained in one or more plastic bags. The bed 28 is supported by legs 31 which stand on the pedestal 9.

It will be evident that the stepped, rotational scanning motion imparted by the Geneva mechanism 10 to the member 1 needs to be synchronised with the lateral scanning motion imparted to the yoke 16 by the reciprocating motor 22 and to this end the member 1 is formed with an annular graticule, part of which is shown at 32, and a fixed photodetector 33 is provided, together with a suitable light source (not shown) to provide timing pulses indicative of the passage of markings on the graticule 32 past the photodetector 33. Thus the rotational scanning motion of member 1 can be monitored, and similarly a linear graticule 34 is fixedly attached to the yoke 16 and co-operates with a second photodetector 35, which is mounted on the member 1 so as to rotate therewith, and a similarly mounted light source (not shown) to produce timing pulses indicative of the progress of the lateral scanning. Both graticules 32 and 34 comprise translucent or transparent members bearing opaque lines printed, etched or otherwise provided thereon. The two sets of timing pulses are fed to a control circuit 36 which controls the motor 22 and the motor (not shown) which drives the disc 13 of the Geneva mechanism 10 in such a way that after each step of rotational motion a single lateral scan is carried out to scan the source 25 and the detectors array 26 in one direction of the other across the aperture 2. Thus a single lateral scan is carried out for each dwell angle of the member 1; these dwell angles being ten degrees apart.

Each detector in the array 26 comprises, for example, a scintillator crystal (e.g. caesium iodide) and an associated photomultiplier tube, or a photodiode, and thus provides electrical signals indicative of the amount of radiation detected thereby. The electrical signals so provided are applied to respective preprocessing circuits 37, each of which contains an amplifier 38, a resettable integrator 39, and analogue-to-digital converter circuit 40 and a logarithmic converter circuit 41. The integrators 39 are read and reset synchronously and periodically by means of timing pulses derived from the photodetector 35; the arrangement being such that the reading and re-setting occurs some one hundred and sixty times during each lateral scan in either direction. Thus, during a single lateral scan, output signals are provided which are indicative of the absorption suffered by the X-radiation on traversing a set of one hundred and sixty parallel paths from the source to the detector at each of thirty angular orientations with respect to the body 3. The member 1 is then rotated through ten degrees and a second group of thirty sets of one hundred and sixty output signals are derived. The process is repeated until the member 1 has been rotated through at least 170° and all of the output signals obtained during the scanning are processed in a processing circuit 42 to evaluate the absorption coefficient, with respect to the radiation used, at a plurality of locations distributed over the slice of the body 3 which lies in the plane of the beam of X-rays generated by the source 25.

Preferably the processing is carried out in accordance with the technique described and claimed in the aforementioned U.S. Pat. No. 3924129. As previously mentioned, this technique involves a form of convolution and preferably the output signals are assembled in sets relating to parallel paths through the body. Each output signal is then modified by combining it with components of other output signals of its own set; the weighting being in accordance with a function which is negative, and decreases in amplitude as the distance from the path giving rise to the output signal being weighted to the path giving rise to the output signal being modified increase. The modified output signals are then additively combined in accordance with the inter relationships of the paths to which they relate, in accordance with a layergramming procedure, the modification of the output signals being such as to compensate for the known inaccuracies of conventional layergrams.

It is usual to evaluate the absorption coefficients for regions distributed in a regular matrix type array over a region, such as that indicated by a circle 43 in FIG. 1, which includes the particular part of the body 3 which is to be examined. The modification of the output signals is effected only in respect of beam paths lying in this circle 43 and it has been assumed hitherto that parts of the body 3 which lie outside the circle 43 have no deletrious effects on the accuracy of the evaluation. However it has now been discovered that the above assumption is not always justified. It will be appreciated that the radiation which is projected through the circle 43 along at least some of the paths referred to above also passes through the parts of the body 3 which lie in a zone outside the circle and hence, if substantially absorbing material exists in the zone of the body 3 outside circle 43, this can affect the output signals produced in respect of the relevant paths.

In accordance with this example of the invention, and as will be explained with reference to FIG. 2, additional output signals are derived during each lateral scan from one of the detectors, the sixteenth in this case, in respect of paths which are wholly outside the circular region 43. These additional output signals are used in the convolution process, being suitably weighted in accordance with the aforementioned function and combined with the output signals relating to paths inside, but adjacent the extremity of, the circular region 43. The same additional output signals (i.e. those derived from the sixteenth detector) are used for all thirty sets of output signals derived during the lateral scan in question; thus the sets of additional output signals are spaced by ten degrees from one another.

In FIG. 2, one set of paths giving rise to a set of additional output signals is shown at $44_a$, and $44_b$, whilst part of a second set of paths giving rise to an adjacent set of additional output signals is shown at 45.

The fan beam of X-radiation is shown at 46, where the disposition of the various detectors in the array 26 can be seen. As has been mentioned, the fan has an angular spread of 10°, with the array 26 including thirty detectors inclined at $\frac{1}{3}$° to one another. The Figure shows that the fan beam 46 is slightly asymmetrical about the perpendicular from the effective point source to the detector array, the said perpendicular being arranged to intersect the sixteenth detector D16 (counting from the left). Thus, there are fifteen detectors to the left of the said perpendicular and fourteen to the right thereof. This is done because if the fan 46 were symmetrical about the perpendicular and the array contained thirty one detectors, the extra detector would merely produce output signals which would duplicate those produced by the first detector, D1, during the succeeding or preceding lateral scan. A path which would have been investigated by such a detector is shown at 47 in dashed lines.

Since the additional output signals relating to paths such as 44 and 45 are merely used to supplement the convolution process, it is not necessary that they should be of the same high resolution as the output signals relating to paths which traverse part of the circular region 43. If desired, therefore, groups of output signals relating to adjacent paths in sets such as 44 can be combined and averaged to produce lower resolution signals for use in supplementing the convolution process. Of course the process has to be suitably arranged to cope with the change in resolution, and this may be dealt with either by treating the averaged values as lump values which are attributable to the central beam path of a group, other beam paths of the group being ignored, or by assigning the same averaged value to each beam path of a group.

Clearly the invention may be implemented in a number of different ways. For example the additional output signals need not be derived from detector D16; they could be derived instead from detector D1, for example. Furthermore the additional output signals need not be derived from the same detector during each lateral scan. Moreover the additional output signals can be derived from more than one detector during each lateral scan.

Additional refinements may be made to the apparatus shown in FIG. 1 without departing from the scope of the invention. For example blocks of X-ray absorbent material could be disposed between the source 25 and the body 3 and between the body 3 and the detector array 26 to tend to reduce variations in the degree of absorption suffered by the radiation on traversing paths of different lengths through the body 3. Moreover, the blocks may be arranged to impart a specified attenuation to the radiation when it traverses paths wholly outside the body and its supporting bed so as to permit the sensitivities of the various detectors to be monitored. In this regard, it is advantageous to use the technique, disclosed in the aforementioned U.S. Pat. No. 3946234 in which reference readings for the detectors in one half of the fan-shaped beam of radiation are obtained at one side of the aperture 2 whilst those for detectors in the other half of the beam are obtained at the other side of the aperture 2.

In some circumstances, it can be difficult to physically accommodate the thirty detectors in side-by-side relationship in the array 26 and in such cases it is desirable to stagger the detectors in distance from the source the stagger, of course, being kept to a minimum.

What we claim is:

1. Radiographic apparatus including means for projecting radiation through a slice of a body along a plurality of sets of beam paths, each set of paths being oriented at a respective angle or mean angle in the slice, detector means for detecting the radiation emergent from the body along each path and processing means for processing output signals derived from said detector means and indicative of the absorption suffered by the radiation on traversing each of said paths to evaluate the absorption coefficient, with respect to said radiation, at each of a plurality of locations distributed over a predetermined region of said slice, the apparatus being adapted so that some of said sets, hereinafter termed "extended sets", include more paths than others of said sets; the extended sets being regularly interspersed in angle, or mean angle, with the said other sets and the extra paths in said extended sets traversing a zone of said slice which surrounds said region; the processing means being adapted to utilize the output signals indicative of the absorption suffered by the radiation on traversing said extra paths not only in association with the respective ones of said extended sets in which the extra paths are included but also in association with those of said other sets disposed at less than a given angle, or mean angle to said extended sets to compensate said evaluation for errors introduced by the passage of said radiation through said zone along paths which also traverse said region.

2. Apparatus according to claim 1 wherein said means for projecting includes a source of a substantially planar, fan-shaped beam of the radiation and means for scanning said source relative to said body, and wherein said detector means includes a plurality of detector devices.

3. Apparatus according to claim 2 werein said devices extend across said beam of radiation and said scanning means includes means for scanning said detector means, concomitantly with said source, relative to said body.

4. Apparatus according to claim 2 wherein said scanning means includes means for scanning said source angularly around said body about an axis intersecting said slice.

5. Apparatus according to claim 4 wherein said scanning means includes reciprocable means for scanning said source laterally across said slice, means being provided for synchronising the angular and lateral scanning movements so that a lateral movement is effected between successive angular movements.

6. Apparatus according to claim 2 including means for deriving said further output signals from one only of said detector devices.

7. An arrangement according to claim 1 wherein each said set of paths comprises a plurality of substantially parallel paths.

* * * * *